US012708671B2

(12) United States Patent
Braganhol et al.

(10) Patent No.: US 12,708,671 B2
(45) **Date of Patent: *Aug. 18, 2026**

(54) NANOMETRIC PHARMACEUTICAL COMPOSITION IN THE FORM OF LIPOSOMES OR NANOEMULSION CONTAINING SPECIFIC SEQUENCES OF INTERFERENCE RNA

(71) Applicants: UNIVERSIDADE FEDERAL DO RIO GRANDE DO SUL, Porto Alegre (BR); UNIVERSIDADE FEDERAL DE CIÊNCIAS DA SAÚDE DE PORTO ALEGRE—UFCSPA, Porto Alegre (BR); UNIVERSIDADE FEDERAL DE PELOTAS, Pelotas (BR); UNIVERSIDADE FEDERAL DO PAMPA—UNIPAMPA, Bagé (BR)

(72) Inventors: Elizandra Braganhol, Porto Alegre (BR); Ana Maria Oliveira Battastini, Porto Alegre (BR); Helder Teixeira, Porto Alegre (BR); Marco Antonio Stefani, Porto Alegre (BR); Fernanda Bruxel, Uruguaiana (BR); Roselia Maria Spanevello, Pelotas (BR); Fernanda Cardoso Teixeira, Pelotas (BR); Juliana Hofstatter Azambuja, Porto Alegre (BR)

( * ) Notice: Subject to any disclaimer, the term of this patent is extended or adjusted under 35 U.S.C. 154(b) by 778 days.

This patent is subject to a terminal disclaimer.

(21) Appl. No.: 17/958,671

(22) Filed: Oct. 3, 2022

(65) Prior Publication Data

US 2023/0099345 A1 Mar. 30, 2023

Related U.S. Application Data

(63) Continuation-in-part of application No. 16/964,919, filed as application No. PCT/BR2019/050004 on Jan. 7, 2019, now Pat. No. 11,459,569.

(51) Int. Cl.

| | |
|---|---|
| ***A61K 47/69*** | (2017.01) |
| ***A61K 9/107*** | (2006.01) |
| ***A61K 9/127*** | (2006.01) |
| ***A61K 31/713*** | (2006.01) |
| ***A61K 38/46*** | (2006.01) |
| ***A61K 47/20*** | (2006.01) |
| ***A61K 47/24*** | (2006.01) |
| ***A61P 35/00*** | (2006.01) |
| ***C12N 15/113*** | (2010.01) |
| ***C12N 15/87*** | (2006.01) |
| *B82Y 5/00* | (2011.01) |

(52) U.S. Cl.

CPC ........ *A61K 47/6911* (2017.08); *A61K 9/1075* (2013.01); *A61K 9/127* (2013.01); *A61K 31/713* (2013.01); *A61K 38/465* (2013.01); *A61K 47/20* (2013.01); *A61K 47/24* (2013.01); *A61P 35/00* (2018.01); *C12N 15/1137* (2013.01); *C12N 15/1138* (2013.01); *C12N 15/87* (2013.01); *B82Y 5/00* (2013.01); *C12N 2310/14* (2013.01); *C12N 2320/32* (2013.01); *C12Y 301/03005* (2013.01)

(58) Field of Classification Search

CPC .. A61K 47/6911; A61K 9/1075; A61K 9/127; A61K 31/713; A61K 38/465; A61K 47/20; A61K 47/24; A61K 9/145; A61P 35/00; C12N 15/1137; C12N 15/1138; C12N 15/87; C12N 2310/14; C12N 2320/32; C12N 2320/31; B82Y 5/00; C12Y 301/03005

See application file for complete search history.

(56) References Cited

FOREIGN PATENT DOCUMENTS

BR 132020012751-8 3/2022

OTHER PUBLICATIONS

Azambuja et al. "Nasal Administration of Cationic Nanoemulsions as CD73-siRNA Delivery System for Glioblastoma Treatment: a New Therapeutical Approach". Molecular Neurobiology. 2019.
Azambuja et al. "CD73 Downregulation Decreases In Vitro and In Vivo Glioblastoma Growth". Molecular Neurobiology. 2018.
Azambuja et al. "Inhibition of the Adenosinergic Pathway in Cancer Rejuvenates Innate and Adaptive Immunity." International Journal of Molecular Sciences. 2019.
Azambuja et al. "Blockade of CD73 delays glioblastoma growth by modulating the immune environment." Cancer Immunology, Immunotherapy. 2020.
Azambuja et al. "CD73 as a target to improve temozolomide chemotherapy effect in glioblastoma preclinical model." Cancer Chemotherapy and Pharmacology. 2020.
Teixeira et al. "Development and characterization of CD73-siRNA-loaded nanoemulsion: effect on C6 glioma cells and primary astrocytes." Pharmaceutical Development and Technology. 2020.

*Primary Examiner* — Robert S Cabral
(74) *Attorney, Agent, or Firm* — Cisio & Thomas LLP

(57) ABSTRACT

A nanometric pharmaceutical composition in the form of liposomes or a nanoemulsion containing interference RNA strands comprising one or more of the following specific siRNA sequences: SEQ ID NO: 1; SEQ ID NO: 2; or SEQ ID NO: 3.

20 Claims, 8 Drawing Sheets

Specification includes a Sequence Listing.

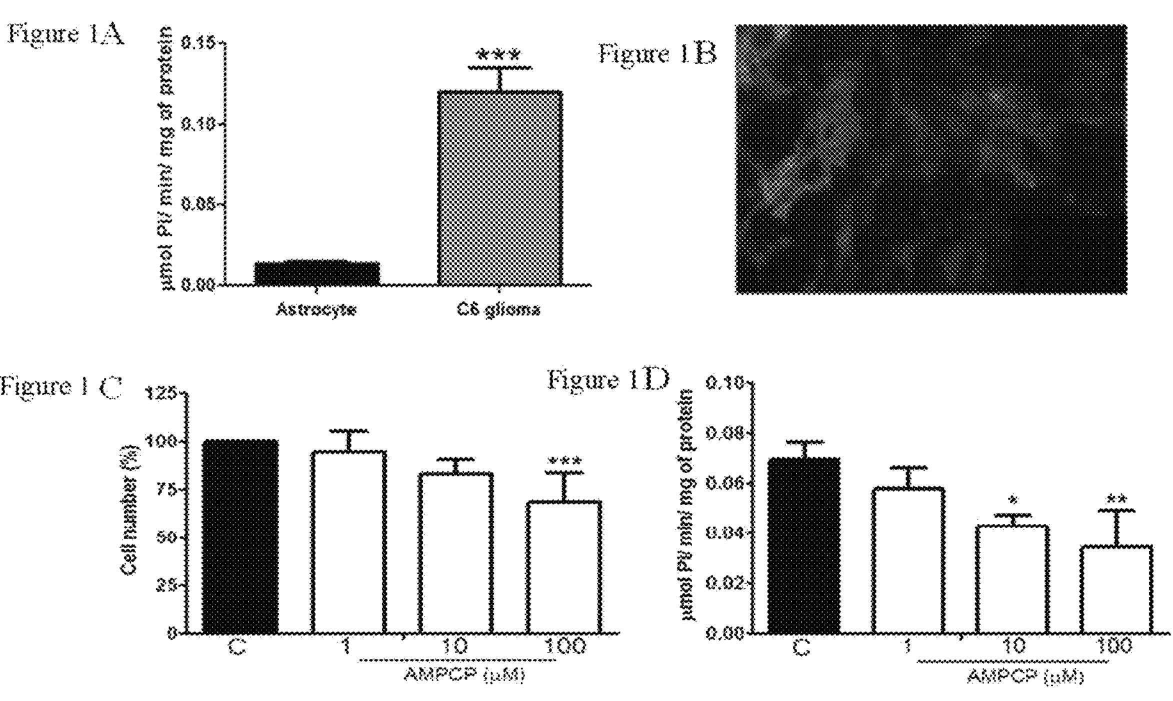
Figure 1A
µmol Pi/ min/ mg of protein
0.15
0.10
0.05
0.00
***
Astrocyte
C6 glioma
Figure 1B
Figure 1 C
Cell number (%)
125
100
75
50
25
0
***
C
1
10
100
AMPCP (µM)
Figure 1D
µmol Pi/ min/ mg of protein
0.10
0.08
0.06
0.04
0.02
0.00
*
**
C
1
10
100
AMPCP (µM)
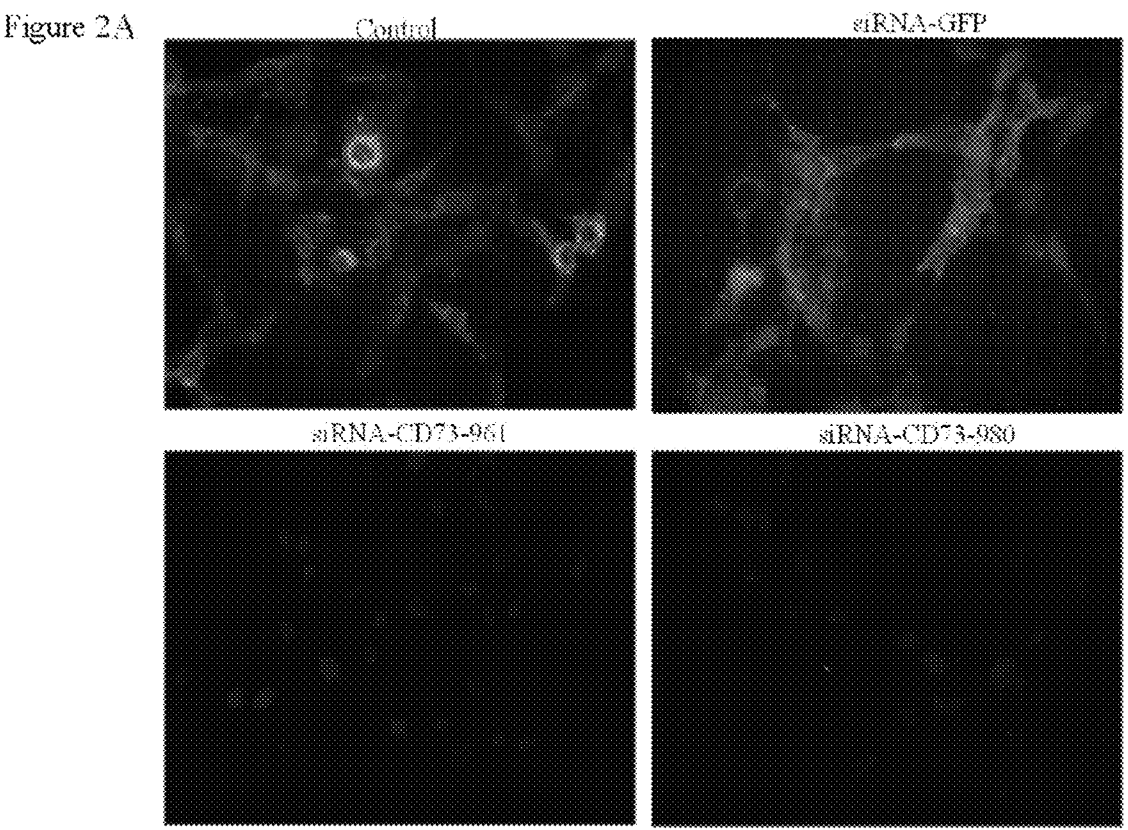
Figure 2A
Control
siRNA-GFP
siRNA-CD73-961
siRNA-CD73-980

Figure 2B
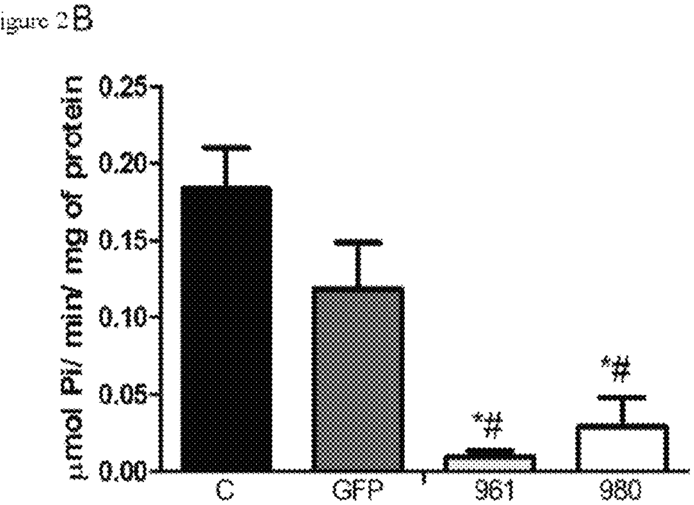
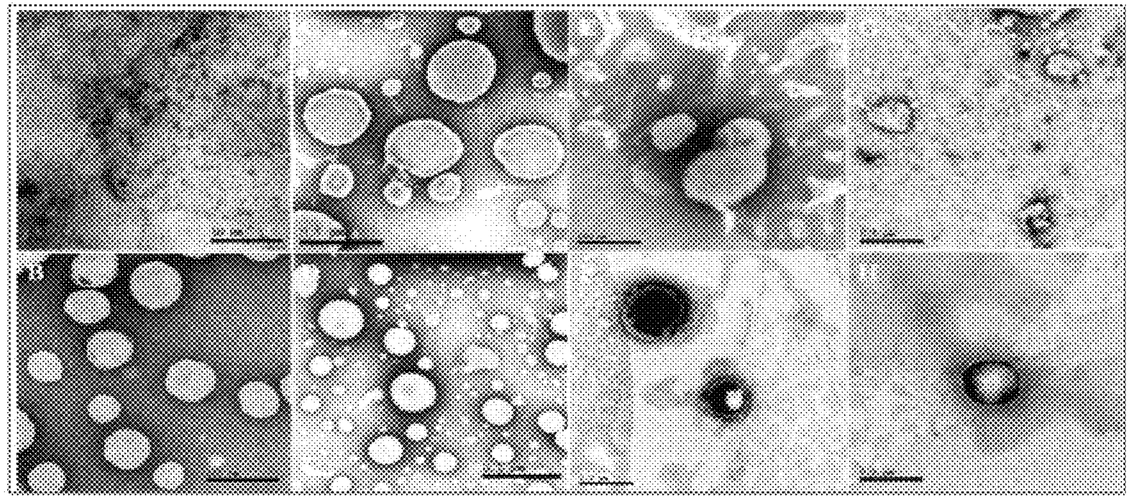
Figure 3

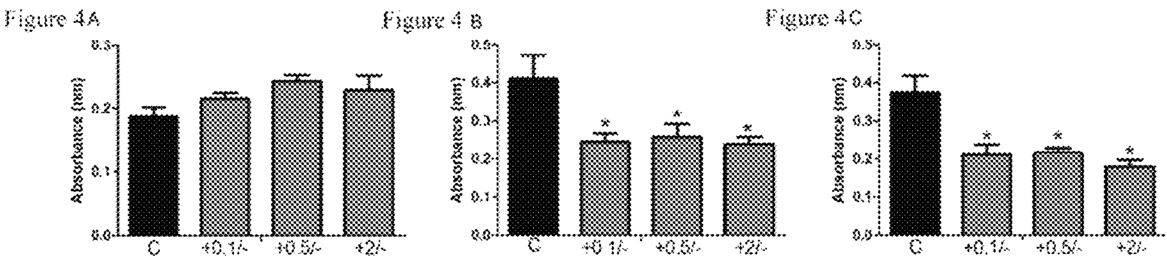
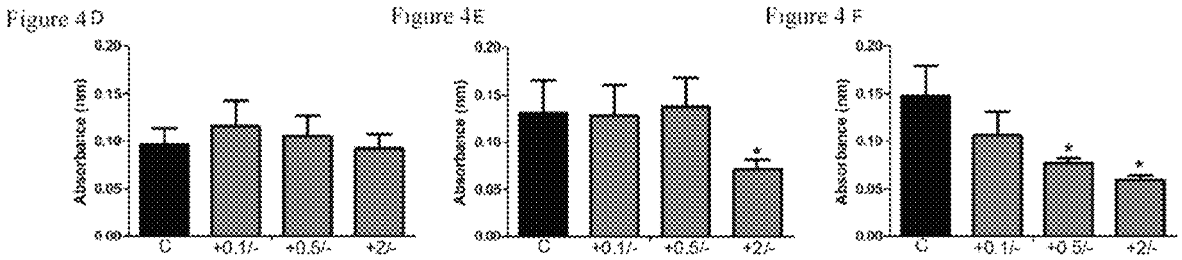
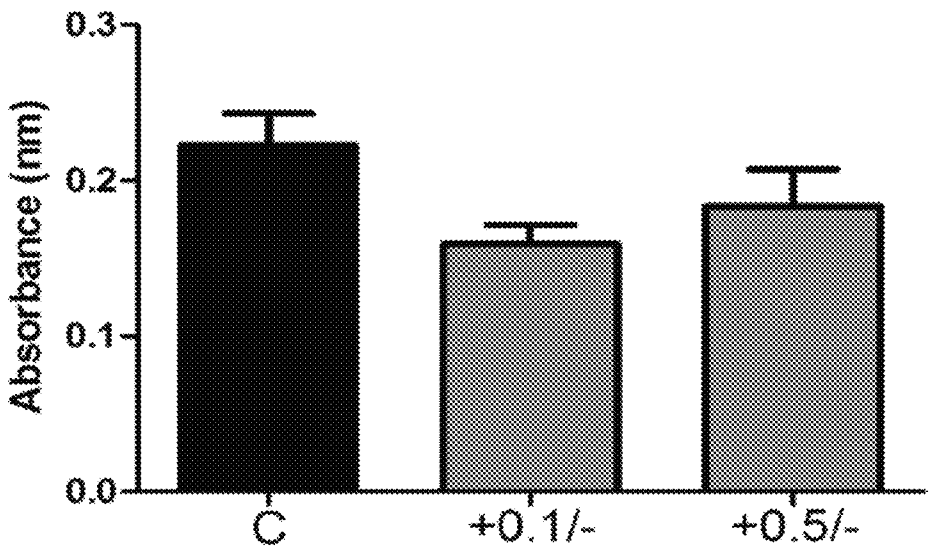
Figure 5

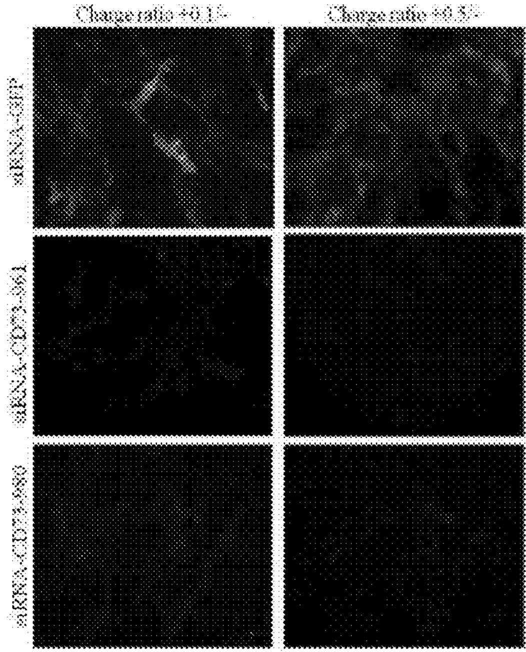
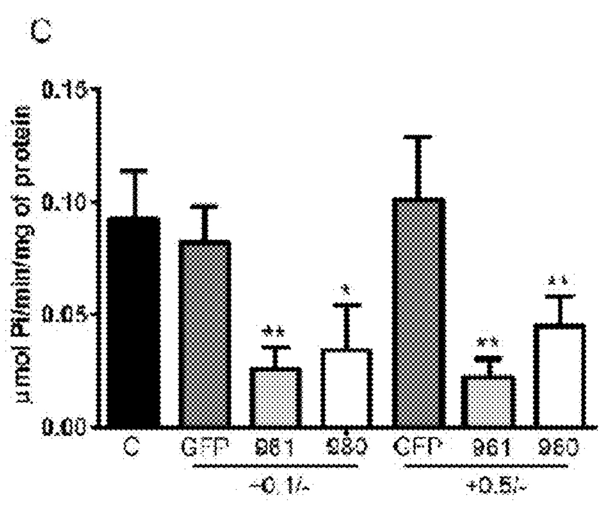
Figure 6
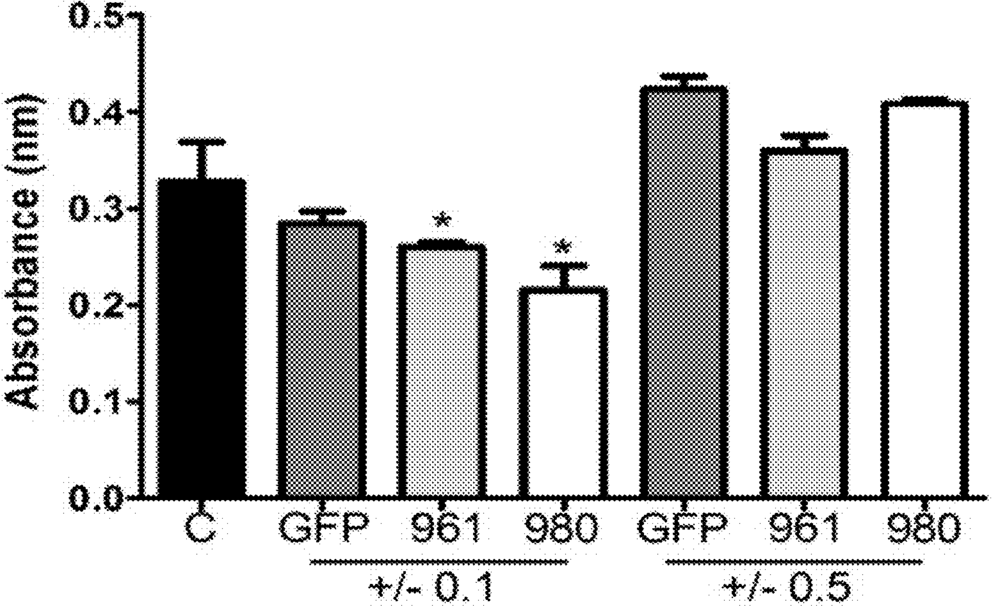
Figure 7

Control NE-siRNA scramble NE-siRNA CD73R

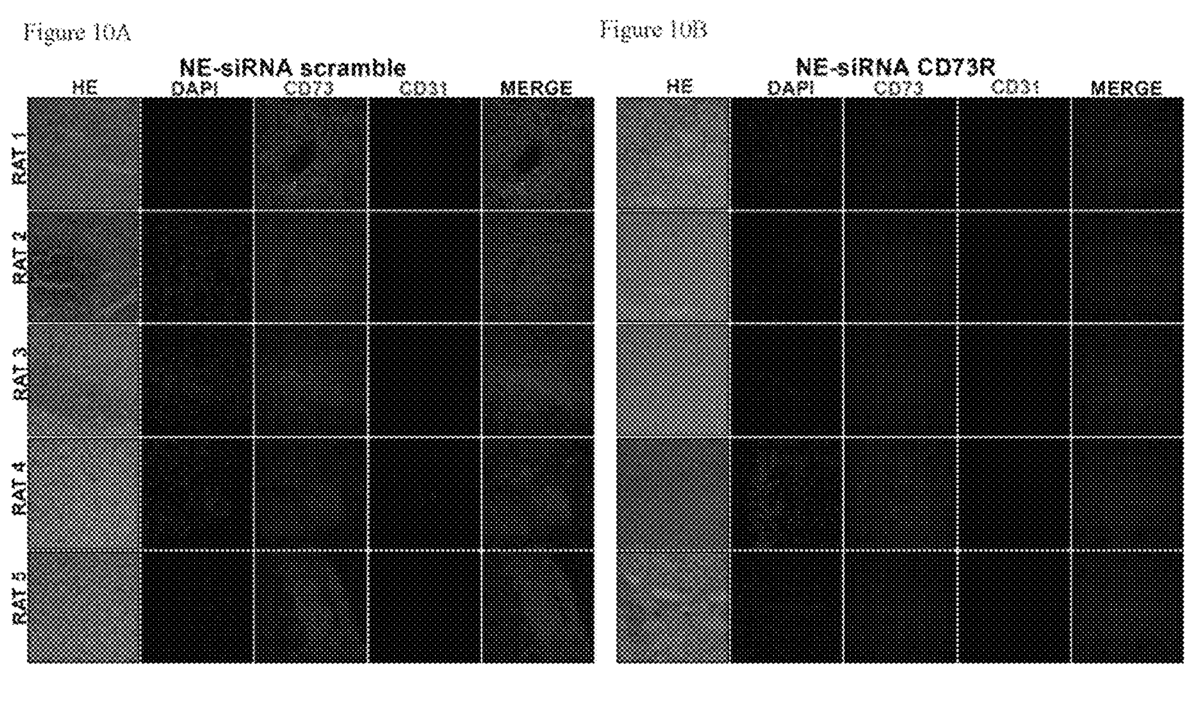
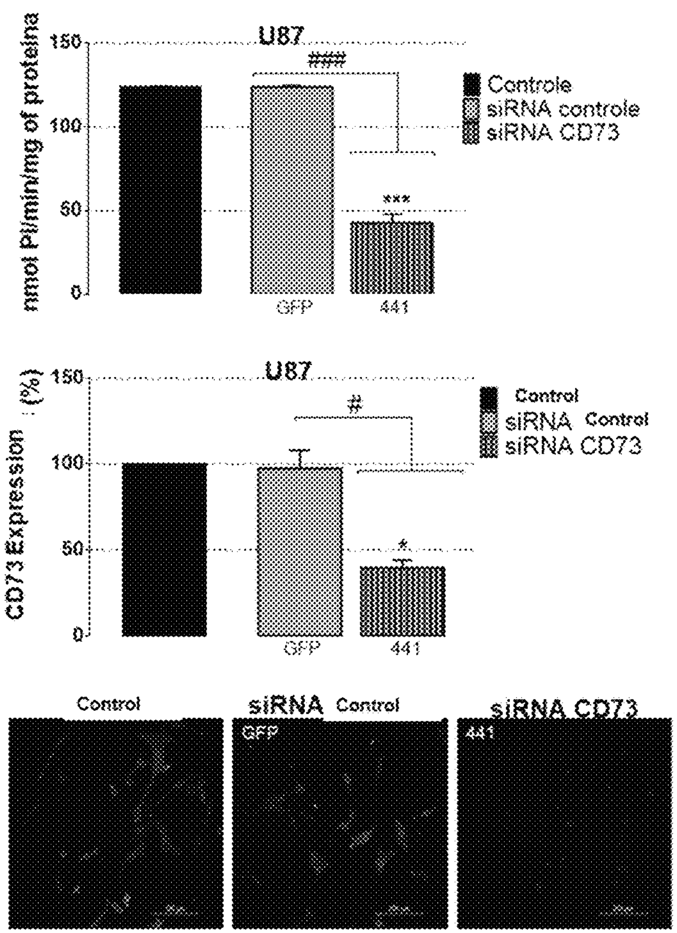
Figure 11

NANOMETRIC PHARMACEUTICAL COMPOSITION IN THE FORM OF LIPOSOMES OR NANOEMULSION CONTAINING SPECIFIC SEQUENCES OF INTERFERENCE RNA

CROSS-REFERENCE TO RELATED APPLICATIONS

This application is a continuation-in-part of U.S. patent application Ser. No. 16/964,919, titled "Nanometric Pharmaceutical Composition in the Form of Liposomes or Nanoemulsion Containing Specific Sequences of Interference RNA," filed Jul. 24, 2020, the contents of which are incorporated by reference herein in their entirety.

SEQUENCE LISTING XML

Applicant hereby incorporates by reference the following XML file: Revised_Sequence_Listing.xml, created on Oct. 19, 2022, having a size of 6000 bytes.

INVENTION FIELD

The present invention is located in the Nanotechnology, Pharmacy and Genetics fields, being related to a nanometric scale composition of interference RNA molecules release capable of silencing genes responsible for the protein expression of proteins and enzymes overexpressed in tumors. The invention composition contains liposomes or nanoemulsions that interact effectively with the interference RNA, forming complexes of site-directed release. The composition provides compatibility with a plurality of pharmaceutical formulations, in addition to being safer than traditional methods.

INVENTION RECORDS

Cancer is a group of diseases that involve abnormal cell growth, with the potential to invade and spread to other parts of the body, in addition to the original location. A cell mass with this abnormal growth is called tumor.

Glioma is a general term for a group of brain tumors that have phenotypic characteristics and gene expression similar to glial cells. Gliomas can be classified according to the malignancy characteristics in grade I, II, III or IV, and grade IV glioma is also known as glioblastoma. Glioblastomas are among the brain tumors with the highest growth rate, invasion and lethality.

Glioblastoma is the most common and aggressive type of malignant brain tumor affecting humans. Initial signs and symptoms are nonspecific and can include headache, personality changes, nausea and stroke-like symptoms. The symptoms worsening are generally rapid, and may progress to unconsciousness. The prognosis for patients with this type of tumor is poor and the average survival time after diagnosis is from 12 to 15 months.

Current treatment methods basically consist of neurosurgery, the use of substances that inhibit tumor growth, either by inhibition of angiogenesis which is necessary to demand resources for this type of tumor, or by the cytotoxic action that prevents replication and, as a consequence, tumor growth.

The neurosurgery to remove tumor cells, despite being an effective treatment method to promote increased of patient survival, has some classic limitations, such as the tumor location and the invasiveness degree. Depending on the region of growth, some tumors may be inoperable, or even operable, but with high surgical risk and/or great post-surgical discomfort for the patient.

The use of substances that inhibit tumor growth also has disadvantages. The first-line substance for the treatment of glioblastoma is temozolomide, an oral chemotherapy and alkylating antineoplastic agent. Despite being a drug with few side effects, it still presents risks, since it is genotoxic and teratogenic. Its effectiveness is also limited due to the speed of tumor replication, and its main use is to increase the patient's survival, since the intrinsic or developed resistance to this chemotherapy is inevitable, resulting in high rates of tumor recurrence and consequent patient death.

Regarding the formulations containing the above mentioned growth-inhibiting substances, temozolomide is presented in oral form and also in intravenous form. Depending on the substance being administered, some disadvantages can also be noticed. In the case of temozolomide, for example, an oral administration must have a dosage capable of minimizing the primary hepatic metabolism, in addition to minimizing the spread into the bloodstream, which would also inhibit the cell division of other healthy cells and generate discomfort, being this disadvantage also present in the intravenous administration. Other drugs may have low bioavailability in the central nervous system due to the blood-brain barrier presence, being ineffective for the treatment of glioblastoma, as it occurs in the brain.

To be ideal, an antineoplastic formulation should be able to deliver only the effective amount of the chemotherapy at the specific site of action, in addition to being able to cross the blood-brain barrier and be easy to administer.

Besides the toxicity of the chosen chemotherapeutic target must be rigorously analyzed. Ideally, the chemotherapy should be effective only on tumor cells, selectively inhibiting cell replication.

However, most current antineoplastic formulations have systemic action and carry high doses of toxic chemotherapeutic substances, bringing significant side effects for patients.

The present invention aims to address all the problems explained above. The invention comprises a system of liposomes or nanoemulsion, containing a specific and effective amount of chemotherapy with genetic action. The invention uses interference RNA strips capable of silencing the gene responsible for the transcription of the adhesion protein and adenosine-generating enzyme, a tumor-promoting molecule, ecto-5'-nucleotidase/CD73, overexpressed in several tumors, including glioblastoma.

Thus, the present invention addresses not only a formulation capable of carrying only the effective amount of chemotherapy but a specific agent for tumor characteristics.

INVENTION BACKGROUND

The file WO 2004/079013 describes a method of diagnosing and predicting the stage of pancreatic cancer which comprises detecting the expression and activity of the ecto-5'-nucleotidase protein in a sample of cancer cells and comparing the results with normal cells. The document also reports compositions for the tumor treatment containing fragments of interference RNA, and that these compositions can be liposomes and emulsions. However, there is no mention of the treatment of glioblastomas or the nanometric size of the formulations.

The file PI 0709506-6 describes the use of interference RNA for inhibiting the expression of spleen tyrosine kinase mRNA (SYK), particularly for the treatment of patients who have a SYK-related inflammatory condition or are at risk of developing a related inflammatory condition, such as allergic conjunctivitis, eye inflammation, dermatitis, rhinitis, asthma, allergy, or mastoid cell disease.

The file PI 0619738-8 describes isolated interference RNA (siRNA) sequences, comprising a strand of sense RNA and a strand of complementary antisense RNA, which together form a duplex of RNA, with fragments of 14 to 30 nucleotides contiguous to the nucleotide sequence of the exon F of the gene encoding the protein myosin V. The document also describes compositions comprising at least one siRNA and the use of at least that siRNA as a cosmetic or therapeutic agent for skin depigmentation.

The scientific paper "Anti-CD73 antibody therapy inhibits breast tumor growth and metastasis", published in the Proceedings of the National Academy of Sciences of the United States of America (PNAS) on Jan. 26, 2010, describes, as the title implies, the development of a selective monoclonal antibody to the ecto-5'-nucleotidase adhesion protein, which is overexpressed in breast tumors.

Thus, none of the above describes, at the same time, a liposome/nanoemulsion system, containing specific interference RNA fragments, and used to inhibit the activity of the adhesion protein and extracellular adenosine-generating enzyme, ecto-5'-nucleotidase, in glioblastoma.

Due to all the information/limitations shown above, the inventors sought and developed the present invention, which provides solutions to several technical problems already presented. This document describes antineoplastic nanometric formulations, which aim to overcome several of the problems mentioned above and promote safety and efficacy in the treatment of glioblastoma.

INVENTION SUMMARY

The present invention relates to a nanometric scale formulation containing interference RNA strands capable of silencing genes that regulate the expression of overexpressed adhesion proteins and the formation of adenosine in some types of tumors.

First, the present invention provides a nanometric composition consisting of liposomes or nanoemulsions containing strands of interference RNA.

Second, the present invention provides the use of the described composition to silence genes that regulate the expression of overexpressed proteins in tumors.

As a third aspect, the present invention presents a complex of liposomes or nanoemulsion with the interfering RNA capable of crossing the blood-brain barrier and being a specific site.

In a fourth aspect, the present invention provides a pharmaceutically acceptable formulation containing the nanometric composition.

In one embodiment, the pharmaceutically acceptable formulation is intratumor injection, intravenous injection or a nasal spray.

These and other aspects, characteristics and advantages of the invention will become even more evident to those skilled in the art from the detailed description below and the attached claims.

BRIEF DESCRIPTION OF FIGURES

FIGS. 1A-1D shows the analysis of ecto-5'-NT/CD73 activity/expression in C6 glioma cells and the effect of AMPCP, an enzymatic inhibitor of ecto-5'NT/CD73, on cell proliferation.

FIGS. 2A-2B shows the evaluation of ecto-5'-NT/CD73 silencing by specific siRNA-CD73 sequences.

FIG. 3 shows the morphological characterization of the nanoemulsion (NE)/siRNA-CD73 complexes.

FIGS. 4A-4F shows the optimization of C6 glioma transfection using NE/siRNA complexes.

FIG. 5 shows the cytotoxicity analysis of the NE/siRNAGFP complex in cultures of astrocytes, normal glial cells.

FIG. 6 shows the evaluation of the silencing of the enzyme ecto-5'NT/CD73 by NE/siRNA-CD73 complexes.

FIG. 7 shows the analysis of NE/siRNA-CD73 treatment on cell viability of C6 glioma.

FIGS. 10A-10B shows that treatment with NE-siRNA CD73-980 promotes silencing of CD73 in vivo in a preclinical model of glioblastoma through representative images of immunohistochemistry.

FIG. 11 shows the efficiency of the siRNA-CD73-441 sequence to silence CD73 expression in U87MG lineage of human glioblastoma.

DETAILED DESCRIPTION OF INDUSTRIAL CREATION AND INVENTION

Figures 8, 9:
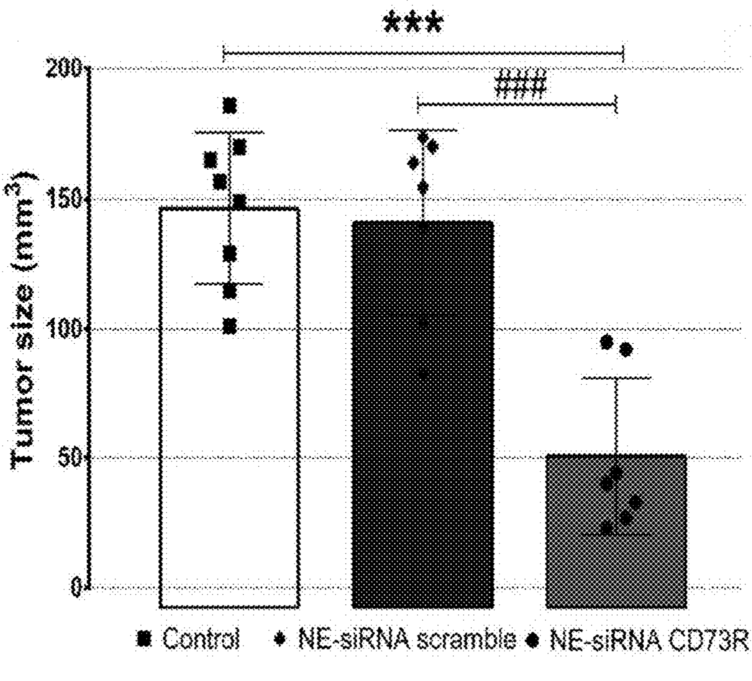
FIG. 8 shows the efficiency of NE/siRNA-CD73-980 treatment in reducing tumor progression in a preclinical model of glioblastoma through the analysis of tumor size quantification.
FIG. 9 shows the efficiency of NE/siRNA-CD73-980 treatment in reducing tumor progression in a preclinical model of glioblastoma through representative images.

The present description aims to deepen the details about the inventive concept, to provide examples that facilitate the cognition/understanding of it and to provide precise technical data about some of the ways to concretize the inventive concept. The detailed description also aims to avoid the repetition, by third parties, of the extensive experimentation, financial investments, time and intellectual activity that the inventors/depositor made to solve the technical problems now solved.

For the avoidance of interpretation doubt, any feature described in one aspect of the present invention can be used in another aspect of the invention. The word "comprising" is intended to mean "including", but not necessarily "consisting of" or "composed only of". In other words, the steps or options listed need not be exhaustive. Note that the examples provided in the description below are intended to clarify the invention, and should not per se be interpreted as limiting the scope of the invention.

In a first aspect, the present invention provides a nanometric pharmaceutical composition comprising liposomes or nanoemulsion containing interfering RNA filaments.

In one embodiment of the nanometric pharmaceutical composition, the interference RNA filaments have a sense and antisense stripe composed of 19 nucleotides in reverse orientation, separated by a space of 1 base pair defined according to SEQ ID No: 1, SEQ ID No: 2, and SEQ ID No: 3.

In one embodiment of the nanometric pharmaceutical formulation, it additionally comprises a pharmaceutically acceptable excipient.

In one embodiment of the nanometric pharmaceutical composition, it is in the form of an intratumoral, parenteral injection or nasal spray.

In a second aspect, the present invention provides the use of said nanometric pharmaceutical composition to prepare a drug to silence genes responsible for the expression of overexpressed proteins in tumors.

In one embodiment of the use, the silenced gene is NT5E (gene ID: 58813; 5'nucleotidase, ecto; *Rattus norvergicus*) and NT5E (gene ID: 4907; 5'-nucleotidase-ecto; *Homo sapiens*).

In one embodiment of the use, the protein to be regulated is ecto-5'-nucleotidase/CD73.

In one embodiment, the tumor is glioblastoma.

In one embodiment of the use, described composition is administered in the form of intratumoral, parenteral injection or nasal spray.

The treatment of glioblastoma remains a challenge for oncology. The therapies currently offered are only palliative and the average survival of diagnosed patients is only 12 months.

Thus, the proposed invention aims to offer a new therapeutic strategy for the treatment of glioblastoma that can also be used for other neoplasms that have not yet been cured or refractory to available treatments.

The therapy target is the enzyme and adhesion protein ecto-5'-nucleotidase/CD73 (CD73). Increased expression and enzymatic activity of this protein has been widely reported in tumor tissues, including glioblastomas, and is associated with increased characteristics of tumor malignancy, such as migration, adhesion, invasion, angiogenesis and escape from the immune system. Thus, strategies to decrease the expression and/or activity of CD73 could be useful for the treatment of glioblastoma and also of other neoplasms that present increased expression of that target.

An innovative way of silencing gene expression is the use of interference RNA (siRNA) sequences for a given target. Interference RNA is a mechanism exercised from two complementary sequences of 19 nucleotides in inverted orientation, unpaired by a space of 1 pair of specific messenger RNA bases, resulting in the inhibition of gene expression in the translation phase or hindering the transcription of specific genes. The final result is a decrease in the expression of the target protein which, in this proposal, is CD73.

Although siRNA technology is very promising, its use in the clinic comes up against some factors such as the difficulty in accessing the central nervous system due to the limitations imposed by the blood brain barrier and the degradation of siRNA sequences by endogenous nucleases.

As a way to get around such problems, siRNA sequences can be administered locally, via intracerebral/intratumoral injections, nasal or systemically, intravenously, using liposomal systems or nanoemulsions as dispensing carriers. Such formulations interact efficiently with siRNA, forming complexes that potentially cross cell and blood-brain barriers and facilitate targeted site release, cell uptake and interaction with the intracellular target of siRNA sequences.

Besides, the use of non-viral vectors such as liposomes or nanoemulsions has been considered a more attractive alternative when compared to viral vectors, due to biosafety aspects.

Briefly, the present invention features a nanometer scale composition, containing liposomes or a nanoemulsion containing specific interference RNA (siRNA) strands, capable of silencing the NT5E (gene ID: 58813; 5'nucleotidase, ecto; *Rattus norvergicus*) and NT5E (gene ID: 4907; 5'-nucleotidase-ecto; *Homo sapiens*).

Effects of siRNA-CD73 on in vitro glioma progression.

Cell Culture and Cell Line: Glioma cell line (C6) was obtained from ATCC (American Type Cell Collection, USA) and were grown in Dulbecco's Modified Eagle's Medium (DMEM), a sterile culture medium containing glucose, L-glutamine and sodium bicarbonate, 5% fetal bovine serum (FBS) in a cell incubator at 37° C. and 5% $CO_2$/95% humidity, according to the standard maintenance protocol for cell cultures.

Primary astrocyte cultures were prepared from scratch. The cortex of newborn Wistar rats (1-2 days old) were removed and mechanically dissociated in a balanced saline solution free of $Ca^{+2}$ and $Mg^{+2}$ (pH 7.4), containing 137 mM NaCl, 5, 36 mM KCl, 0.27 mM $Na_2HPO_4$, 1.1 mM $KH_2PO_4$, and 6.1 mM glucose. After centrifugation at 1000 g for 5 min, the pellet was resuspended in culture medium (pH 7.6) containing 1% DMEM, 8.39 mM of HEPES buffer (4-(2-hydroxyethyl)-1-acid piperazine ethanesulfonic) (pH 7.6), 23.8 mM $NaHCO_3$, 0.1% fungizone® (Amphotericin B, antifungal), 0.032% antibiotic garamycin and 10% FBS. The cells were seeded at a density of $1.5\times10^5$ cells/cm$^2$ at 24-well plates pre-treated with poly-L-lysine. The cultures were also maintained in 5% $CO_2$/95% air at 37° C. Subsequently, the cells were treated with adenosine 5'-(α, βmethylene) -diphosphate (AMPCP, Sigma, USA), a selective inhibitor of CD73 is used to study the regulation of adenosinergic signaling through this protein. AMPCP was dissolved in water at a concentration of 100 mM (stock solution) and subsequently diluted in DMEM 5%/FBS to obtain the concentrations of use (1, 10 and 100 μM). C6 glioma cells ($2\times10^4$ cells/well) were seeded in 24-well plates. After 24 h, cultures were treated with AMPCP for 48 h. Controls were exposed only to the DMEM 5%/FBS medium.

After treatment with AMPCP, the medium was removed, the cells were washed with PBS buffer solution (phosphate buffered saline, solution containing NaCl and $NaHPO_4$), trypsinized with 200 μL of 0.25% trypsin solution and counted in a newbauer chamber. Once the cells were treated, enzyme activity, cell viability and immunocytochemistry assays were performed for CD73, in order to determine the reliability of the tests with the NE/siRNA or Lipofectamine®/siRNA complexes. The enzymatic activity of C6 cells was determined in an incubation medium (2 mM $MgCl_2$, 120 mM NaCl, 5 mM KCl, 10 mM glucose, 20 mM HEPES [pH 7.4], and 2 mM AMP [adenosine monophosphate]) at 37° C. for 10 min, where the inorganic phosphate released by the action of CD73 was measured and the protein concentration was evaluated by the methods of malachite green and Coomassie Blue, respectively. Specific activity was expressed as μmol Pi released/min/mg protein.

In the $5\times10^3$ cell viability assay, C6 glioma cells or primary astrocytes per well were exposed to the NE/siRNA complexes and after 48 hours cell viability was determined by the MTT assay, a colorimetric assay where a yellow tetrazolic compound is reduced to purple formazan in alive cells.

In the immunocytochemistry assay for CD73, C6 glioma cultures were fixed in acetone/formalin solution and washed 3 times for 10 min each with PBS. The cells were incubated with the blocking solution (7% FBS prepared in PBS containing 0.2% Tween-20 [polysorbate, nonionic surfactant]) for 45 min at room temperature. Afterwards, the cells were incubated for 90 min with the primary polyclonal rabbit anti-rat antibody CD73 (glioma C6) (1:1,000) diluted in 7% FBS prepared in PBS containing 0.2% Tween-20. The cells were then incubated with the FITC-conjugated secondary anti-rabbit antibody (affinity-purified antibodies with a well-characterized specificity, providing greater sensitivity through signal amplification, since multiple secondary antibodies can bind to a single antibody primary, fluorescein isothiocyanate conjugate; 1:1,000) for 60 min at room temperature. The images were captured using a digital camera attached to a microscope.

Development of siRNA Sequences for Adhesion Protein and Adenosine-Forming Enzyme Ecto-5'NT/CD73:

The DNA sequences encoding CD73 (gene ID: 58813, *Rattus norvergicus*) were selected to design the siCD73 sequence. All designed sequences were evaluated by BLAST (NCBI) in order to confirm specific homology with the target gene.

Sense and antisense synthetic oligonucleotides formed the template for the generation of an interference RNA sequences composed of two sequences of 19 nucleotides in reverse orientation, unpaired by a space of 1 base pair, defined according to SEQ ID No: 1, SEQ ID No: 2, and SEQ ID No: 3. As siRNA controls absent scramble sequences were used in the genome database.

of siRNA-CD73 sequences in cationic NE, the physicochemical properties of the complexes were determined (Table 2).

The complexes were prepared in three different +/− load ratios (+0.1/−; +0.5/−, +2/− and +4/−). Charge ratios were calculated between the number of positive charges of the cationic lipid present in the NE and the number of negative charges of the phosphate groups of the siRNA sequences.

The average particle size, zeta potential and polydispersion index (PDI) were determined by photon correlation spectroscopy and electrophoretic mobility (Zetasizer Nano ZS, Malvern Instrument, UK), at 20° C. The complex was adequately diluted in water for size and PDI determinations or in 1 mM NaCl solution for zeta potential measurements.

The morphology of the NE/siRNA complexes was also evaluated as described above. The average particle size of the NE varied between 249.9 to 526.52 nm and the PDI varied from 0.1 to 0.6. The zeta potential values of the NE/siRNA complexes were less than zero, resulting in variations in particle size between the preparations. In general, the characteristics presented by the formulations agree with other NE systems reported in the literature.

The polydispersity index tends to increase with the siRNA addition to the nanoemulsion, suggesting a destabilization of the system at lower load rates, and the values were close to

TABLE 1

| siRNA | | Sequences |
|---|---|---|
| GFP (scramble) | Sense | 5'[Phos]rCrArGrGrCrUrArCrUrUrGrGrArGrUrGrUrArUdTdT3' |
| | Antisense | [Phos]rArUrArCrArCrUrCrCrArArGrUrArGrCrCrUrGdTdT3' |
| 961 SEQ ID No: 1 | Sense | 5'[Phos]rGrCrCrArUrCrArArArGrCrArGrArCrArUrUrArArC3' |
| | Antisense | 5'[Phos]rUrArArUrGrUrCrUrGrCrUrUrUrGrArUrGrGrCrUrG3' |
| 980 SEQ ID No: 2 | Sense | 5'[Phos]rArCrCrArGrUrGrGrArGrGrArUrArArArArUrUrArG3' |
| | Antisense | 5'[Phos] rArArUrUrUrUrArUrCrCrUrCrCrArCrUrGrGrUrUrA3' |
| 441 SEQ ID No: 3 | Sense | 5'[Phos]rGrGrGrGrCrCrArCrUrArGrCrArUCrUrCrArArArU3' |
| | Antisense | 5'[Phos] rUrUrGrArGrArUrGrCrUrArGrUrGrGrCrCrCrCrUrU 3' |

Preparation and Characterization of Nanoemulsions (NE):

NE composed of 8% (w/w) medium chain triglycerides, 2% (w/w) egg lecithin, 0.132% (w/w) DOTAP (N-[1-(2,3-dioleoyloxy) propyl] N, N, Ntrimethylammonio-methylsulfate, a liposomal transfection agent), 2.25% (w/w) glycerol and water to complete 100% (w/w) were prepared by spontaneous emulsification. Briefly, an ethanolic solution containing the components of the oil phase was slowly added to the aqueous phase containing glycerol under moderate stirring. The excess of the solvent mixture (ethanol/water) was removed under reduced pressure at 50° C. until reaching the desired final volume (5 ml). The final concentration of cationic lipid was 2 mM, as previously optimized.

Preparation and Characterization of NE/siRNA Complexes:

The adsorption of the siRNA-GFP, siRNA-CD73-961 or siRNACD73-980 sequences in the cationic NE was carried out at the end of the NEs production process, resulting in the formation of the NE/siRNA-GFP, NE/siRNACD73-961 or NE/siRNA-CD73-980. Increasing concentrations of NE were added to aqueous solutions of siRNA sequences (1 μM—final concentration) and incubated for 15 min at room temperature.

NE was chosen as non-viral vectors for the delivery of siRNA-CD73 sequences to specific targets. After adsorption 0.2 only for the NE and +4/− complexes, indicating a homogeneous distribution of these systems.

TABLE 2

| siRNA | Charge ratio | Mean diameter (nm) | Zeta Potential (mV) | Polydispersion Index |
|---|---|---|---|---|
| NE | — | 188.48 ± 25.60 | 45.5 ± 5.13 | 0.1412 ± 0.059 |
| NE/ siRNA- GFP | +0.1/− | 348 ± 12.26 | −42.1 ± 4.12 | 0.302 ± 0.074 |
| | +0.5/− | 323.5 ± 105 | −32.4 ± 10.14 | 0.427 ± 0.154 |
| | +2/− | 294.5 ± 15.05 | −21.5 ± 9.19 | 0.201 ± 0.024 |
| | +4/− | 289.3 ± 13.2 | +4.8 ± 4.3 | 0.25 ± 0.10 |
| NE/ siRNA- 961 | +0.1/− | 526.52 ± 82.99 | −43.69 ± 9.30 | 0.67 ± 0.07 |
| | +0.5/− | 350.46 ± 80.41 | −34.98 ± 17.61 | 0.54 ± 0.14 |
| | +2/− | 272.1 ± 6.724 | −32.5 ± 0.96 | 0.236 ± 0.051 |
| | +4/− | 262.7 ± 12.8 | +3.5 ± 3.0 | 0.23 ± 0.11 |
| NE/ siRNA- 980 | +0.1/− | 414.8 ± 106.8 | −41.7 ± 3.38 | 0.646 ± 0.093 |
| | +0.5/− | 307.4 ± 66.62 | −26.7 ± 3.98 | 0.419 ± 0.175 |
| | +2/− | 249.9 ± 16.33 | −25.9 ± 8.44 | 0.164 ± 0.036 |
| | +4/− | 273.9 ± 13.6 | +0.5 ± 2.7 | 0.19 ± 0.08 |

For adsorption studies, the NE/siRNA-CD73-961 or 980 complexes were prepared in two different charge ratios (+0.1/−; +0.5/−) and transmission electron microscopy was performed (FIG. 3). The analysis revealed that the oil droplets with a typical appearance of an oil/water emulsion present drops of an approximate size of 250-500 nm, according to the physical-chemical characterization. Interestingly, the NE/siRNACD73-961 or 980 complexes showed high electronic density at the interface (FIG. 3, frames C-H). It is well established that oligonucleotides interact with uranyl acetate, resulting in regions of dark shading. These data indicate that the siRNA-CD73 sequences were adsorbed on the NE interface.

Qualitative assessment of the efficiency of siRNA complexation was performed using an agarose gel delay assay. This assay is based on the principle of binding efficiency when from siRNA to DOTAP at the NE interface, the higher the efficiency the more the siRNA migration through the gel will be delayed. The complexes were subjected to electrophoresis for 15 min on 1% agarose gel and then stained with SYBR® Gold (Invitrogen, Carlsbad, USA). Only complex siRNAs with a charge rate of +4/− were completely retained at the application site, and the complexation rate was 80 to 100% for all complexes at the charge rates +2/− and +4/− (data not shown). Therefore, considering the efficiency of oligonucleotide sequence complexation, these load rates (+2/− and +4/−) were applied in subsequent experiments in in vivo experiments.

Cell Transfection Procedures:

Transfection is the process of intentional introduction of nucleic acid into cells. Transfection of the C6 glioma with siRNA sequences (siRNA-GFP, siRNA-CD73-961 or siRNA-CD73-980) was performed using Lipofectamine® (Lipofectamine RNAiMax, Invitrogen), a transfection agent used to specifically increase the efficiency of RNA lipofection in C6 glioma cultures seeded in 24-well plates and with approximately 70% confluence according to the manufacturer's instructions.

For the transfection of C6 cells with the NE/siRNA complexes, the complexes were prepared as described above and the C6 glioma cells were transfected using the forward and reverse protocol. For the direct protocol, $2\times10^4$ C6 cells were seeded in 24-well plates and the transfection mixture was prepared and the cells added the day after sowing. For the reverse protocol, the complexes were prepared inside the well of the 24-well culture plate and, afterwards, $2\times10^4$ C6 glioma cells in culture medium were added. C6 cells were exposed to the complexes for 24, 48 or 72 h.

Effects of siRNA-CD73 on Glioma Progression in vivo:

Preclinical model of glioma and silencing of the CD73 gene in vivo: C6 glioma cells were maintained in culture until they reached approximately 90% confluence. Subsequently, the cells were prepared and a total of $10^6$ cells in 3 μL DMEM/10% FBS were injected into the right striatum, at a depth of 6.0 mm (coordinates in relation to the bregma, 3.0 mm lateral and 0.5 posterior), male Wistar rats (250-300 grams, 8 weeks old) anesthetized by intraperitoneal administration of ketamine and xylazine. Five days after the implantation of the glioma, the animals were randomly divided into three groups: (1) Control (treated with PBS); (2) Scramble-GFP-siRNA (GFP siRNA/nanoemulsion complexes at +4/−1 charges ratio), this group represents a more refined negative control of the experiment, as siRNA scrambled sequences are used; and (3) NE/siRNA-CD73-980 (CD73 siRNA complexes in nanoemulsion at +4/− charges ratio). The formulations were administered nasally every 12 hours, in doses of 10 μg/kg for 15 days.

At the end of the protocol (20 days after implantation of the glioma), the animals were euthanized and the brains were removed, sectioned and frozen. The frozen tissue was later stained with hematoxylin and eosin, and at least 3 sections of each animal were analyzed by a pathologist blinded to the experiment. To quantify the size of the tumor, images of the 3 sections of each brain were captured using a digital camera connected to the microscope (Olympus BX-51, Tokyo, Japan) and the tumor area ($mm^2$) in each slice was determined using the software ImageJ. To calculate the tumor volume ($mm^3$) present in each slice, the calculated area ($mm^2$) was multiplied by the thickness (mm) of each cut. The total tumor volume was obtained from the sum of the tumor volume present in each of the 3 slices. The data were expressed as $mm^3$.

For immunohistochemistry analysis, tissue cuts were performed in cryostat at a thickness of 5 μm. To fix the tissue, a solution containing 95% acetone and 5% formalin was used, and for blocking unspecific markings, a solution containing 1% albumin was used. For analysis, sections were incubated overnight at 4° C. with the following specific antibodies: mouse anti-mouse CD31/PECAM-1 (1:30, 550300, BD Pharmingen, BD Biosciences, Mountain View, USA) and rabbit anti-mouse CD73 (1:2,000; http://ecto-nucleotidases-ab.com). Subsequently, the sections were incubated with the fluorescent secondary anti-mouse Alexafluor 594 antibodies (1:1000, A-21236, Molecular Probes), Alexafluor 488 anti-rabbit (1:500, A11008, Molecular Probes Oregon, USA) and stained with DAPI (4', 6-diamine-2-phenylindole dihydrochloride) (1:10,000) for 15 min. All immunohistological evaluations were performed on tumor fields chosen at random in a 200-fold magnification (Olympus BX-51, Tokyo, Japan).

All procedures used in this study followed the NIH Laboratory Animal Care Principles and were approved by the Ethics Committee of the Federal University of Health Sciences of Porto Alegre (protocol number 293/14).

All results were expressed as mean±standard deviation and statistical analyzes were performed using Analysis of Variance (ANOVA) followed by Tukey's post-hoc (Prism GraphPad Software, USA), considering $p<0.05$ as statistically significant.

EXAMPLES

Example 1

The Selective Ecto-5'-NT/CD73 Inhibitor, AMPCP, Decreases Cell Proliferation of C6 Glioma The activity of ecto-5'-nucleotidase/CD73 was analyzed in C6 glioma cells compared to astrocytes, which was used as an untransformed cell model.

Unlike astrocytes, glioma C6 showed a high AMPase activity (0.013±0.001 versus 0.12±0.01 μmol Pi/min/mg of protein, for astrocytes and C6 cells, respectively; FIG. 1, table A), which was followed up by a high expression of ecto-5'nucleotidase/CD73 on the surface of tumor cells (FIG. 1, panel B).

Thus, it was evaluated how much the selective ecto-5'nucleotidase/CD73 inhibitor, AMPCP, could affect the proliferation of C6 glioma cells. The cells were exposed to increasing concentrations of AMPCP (1, 10 and 100 μM) and after 48 h cell proliferation was determined by counting in a newbauer chamber. In parallel, the activity of the enzyme ecto-5'nucleotidase/CD73 was analyzed by measuring the hydrolysis of AMP to adenosine (ADO) using the malachite green method.

The C6 glioma treatment with AMPCP (100 μM) resulted in a 30% decrease in cell proliferation when compared to the control (FIG. 1, panel C). In addition, treatment with 10 μM and 100 μM AMPCP reduced the AMP hydrolysis by 40 and 50%, respectively (FIG. 1, panel D).

These data indicate that CD73 is overexpressed in gliomas and that its pharmacological inhibition is important to reduce the proliferation of tumor cells.

Example 2

New siRNA-CD73 Sequences are Efficient in Reducing Ecto-5'-Nucleotidase/CD73 Expression in Glioma Cells As the increase in ecto-5'-nucleotidase/CD73 expression is a positive factor for tumor development, including glioblastoma (FIG. 1), a second embodiment was the finding that this enzyme silencing using Interference RNA could be an interesting strategy to control the progression of gliomas.

For this purpose, specific siRNA-CD73 sequences were developed (siRNA-CD73-961 and siRNA-CD73-980; Table 1) and their functionality/specificity was assessed by transfecting C6 cells using Lipofectamine® according to the manufacturer's instructions. After 48 h of transfection, CD73 expression and enzymatic activity were evaluated by immunocytochemistry and AMP hydrolysis, respectively.

Cells transfected with siRNA-GFP sequences were used as controls. As shown in FIG. 2, siRNA-CD73 sequences were efficient in reducing AMP expression (FIG. 2, panel A) and hydrolysis (FIG. 2, panel B) when compared to the control and the cells transfected with the siRNA-GFP sequences. Furthermore, the transfection process per se did not induce cytotoxicity in cells.

These results indicate that the designed siRNA-CD73 sequences were efficient and specific in reducing CD73 expression and activity in C6 glioma and were subsequently used for the development of nanoemulsions (NE).

Example 3

NE/siRNA Complexes are Not Cytotoxic for Primary Astrocyte Culture

Considering that cationic NE has been associated with toxicity in biological systems, the C6 glioma transfection protocol has been optimized with the aim of equalizing high transfection rate and low toxicity.

For this purpose, NE/siRNA-GFP complexes were prepared in three different charge ratios (+0.1/−; +0.5/−; +2/−) and C6 cells were transfected using the forward and reverse protocols, as described in materials and methods. After 24, 48 and 72 h of exposure, cell viability was determined by MTT (FIG. 4, panels A-F).

Direct transfection resulted in 50% C6 glioma toxicity after 48 and 72 h of exposure to the complexes when compared to untreated cells (FIG. 4, panels A-C). For reverse transfection, exposure of C6 cells to the NE/siRNA-GFP complexes at +0.1/− and +0.5/− charge ratios for 48 h did not alter cell viability (FIG. 4, panel E), while exposure by 72 h resulted in 50% toxicity for +0.5/− and +2/− load ratios (FIG. 4, panel F). Together, these data indicate that the reverse transfection protocol resulted in less toxicity when compared to the direct protocol. Then, the NE/siRNA-GFP complexes in two load ratios (+0.1/−; +0.5/−) and the reverse protocol for 48 h of exposure was used in the subsequent experiments.

Finally, the toxicity of the NE/siRNA complexes was also evaluated in astrocytes, a non-tumor glial cell model. Astrocytes were exposed to the NE/siRNA-GFP complexes (+0.1/−; +0.5/−) for 48 h and cell viability was determined by MTT. Notably, the complexes did not promote toxicity to astrocytes when compared to the control, indicating the safety of the formulations (FIG. 5).

Example 4

The NE/siRNA-CD73 Complexes are Efficient in Silencing Ecto-5'-Nucleotidase/CD73 Expression and Activity in C6 Glioma After the physical-chemical characterization and the optimization of the transfection, the effectiveness of the NE/siRNA-CD73-961 and NE/siRNA-CD73-980 complexes in silencing CD73 in C6 glioma was analyzed through immunocytochemical and AMP hydrolysis experiments.

CD73 expression was significantly lower in cells exposed to the NE/siRNA-CD73-961 and NE/siRNA-CD73-980 complexes when the transfected cells were compared with the scramble sequences (NE/siRNAGFP) (FIG. 6, panels A and B). Similarly, AMPásica activity was reduced in silenced cells (reduction of 70% and 63% for siRNA-CD73-961 and siRNA-CD73-980, respectively; FIG. 6, panel C). Thus, the NE/siRNA-CD73-961 and 980 complexes were efficient and selective in silencing CD73 in C6 glioma.

In addition, transfection of C6 cells with the NE/siRNACD73-961 and 980 complexes at +0.1/− charge ratio resulted in a 20 and 35% reduction in cell viability, respectively (FIG. 7). In general, these data suggest that cationic NE were efficient in delivering siRNA-CD73 sequences to C6 glioma cells and that CD73 is an interesting target for the treatment of gliomas.

Example 5

Treatment with NE/siRNA-CD73 Reduces the Growth of Glioblastoma in an in vivo Experimental Model As previously described, glioma cells were transplanted into the brain of the animals in the study, and after 5 days treatment with NE/siRNA-CD73-980 was started for an additional 15 days (10 μg/kg; 12/12 h). Treatment with NE/siRNA-CD73-980 reduced the tumor volume by 60% (58.8±32.7 $mm^3$) when compared to the control groups (139.8±33.5 $mm^3$ and 139.7±35.4 $mm^3$ for the PBS and scramble-GFP-siRNA group, respectively) (FIGS. 8 and 9).

Example 6

Treatment with NE/siRNA-CD73 reduces CD73 Expression in vivo in an Experimental Model of Glioblastoma To determine whether the antiglioma effect of NE-siRNA-CD73-980 was related to CD73 silencing in vivo, CD73 expression was determined by immunohistochemistry in the tumor tissue of animals in the control group or treated with NE-siRNA-CD73-980 (FIG. 10). First, it is interesting to note the greater expression of CD73 in the tumor volume when compared to the adjacent brain tissue. Treatment with NEsiRNACD73-980 led to a decrease in the expression of CD73 in rats with glioma when compared to the control, confirming the ability of the formulation to deliver sequences of CD73 siRNA, resulting in silencing of CD73 in vivo. In addition, qualitative analysis indicates a decrease in CD31/PECAM-1 positive cells, which is suggestive of decreased angiogenesis in animals treated with NE-siRNA-CD73-980 when compared to control.

Example 7

The siRNA-CD73-441 Sequences are Efficient in Silencing CD73 in Human Glioblastoma Lineage U87MG, which Results in Inhibition of Proliferation, Cell Migration and Sensitization to Temozolomide The siRNA-CD73-441 sequence to silence human CD73 was evaluated for its efficiency. The data presented in FIG. 11 demonstrate that the sequence is efficient in decreasing CD73 enzymatic activity (~90%) and protein expression.

Figure 12:
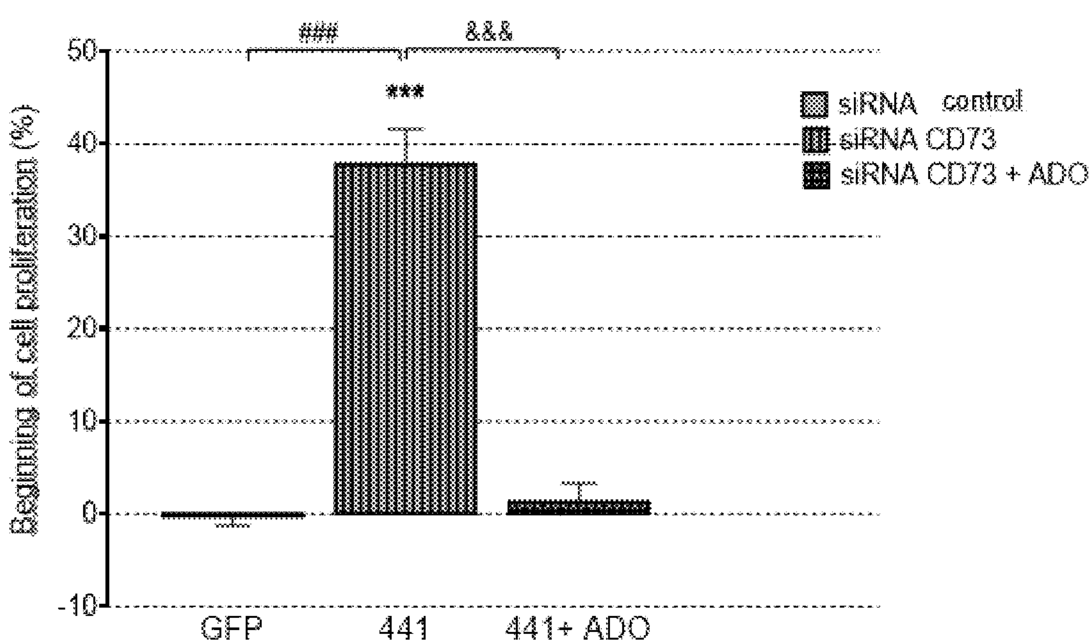
FIG. 12 shows the efficiency of the siRNA-CD73-441 sequence to inhibit cell proliferation of the human glioblastoma lineage U87MG.

To assess the impact of CD73 silencing on U87MG glioma cell proliferation in culture, cells were silenced using the siRNA-CD73-441 sequence and counted using a Neubauer chamber. CD73 silencing resulted in ~40% inhibition of U87MG cell proliferation and ADO treatment restored proliferation in these cells to a level close to control (FIG. 12).

Figure 13:
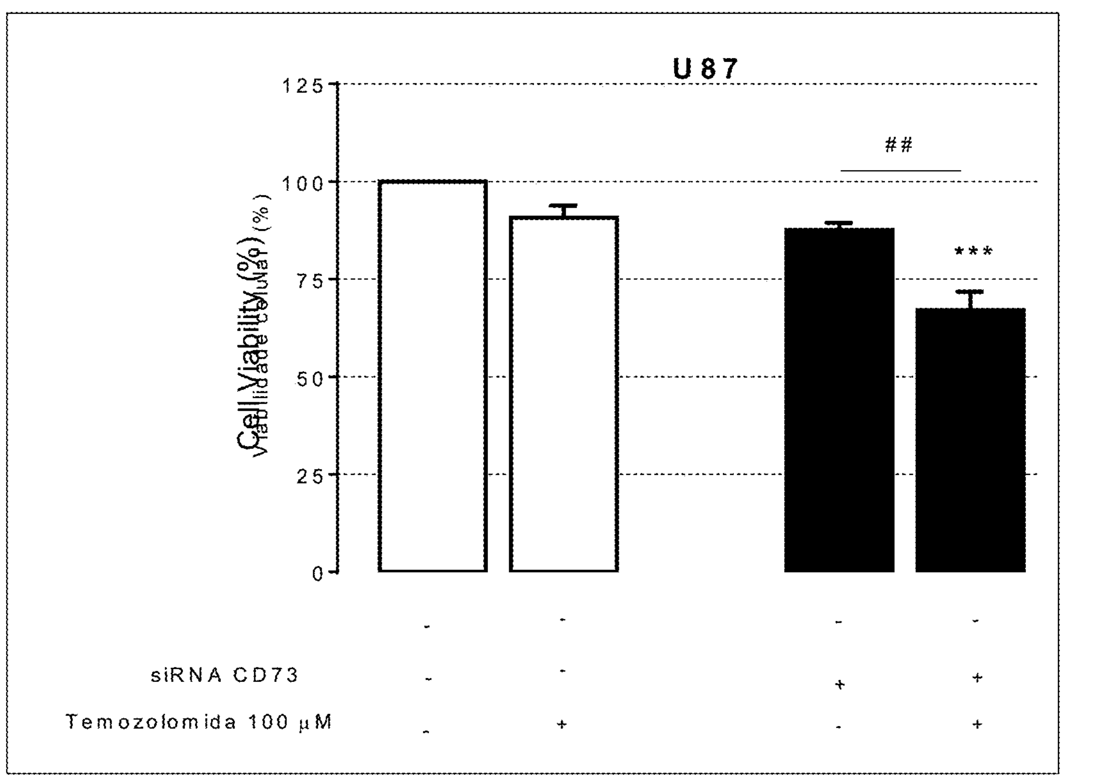
FIG. 13 indicates that CD73 silencing using the siRNA-CD73-441 sequence potentiates the cytotoxicity of temozolomide, a standard chemotherapy drug used for the treatment of glioblastoma, in the U87MG human glioblastoma lineage.

The participation of CD73 in chemoresistance was also investigated (FIG. 13). U87MG glioma cells were treated with temozolomide (100 μM) alone or in combination with siRNA-CD73-441. Temozolomide reduced cell viability by an average of 20% in glioma previously silenced for CD73. Taken together, these data indicate that CD73 inhibition potentiates TMZ cytotoxicity in human glioblastoma cells.

Figure 14:
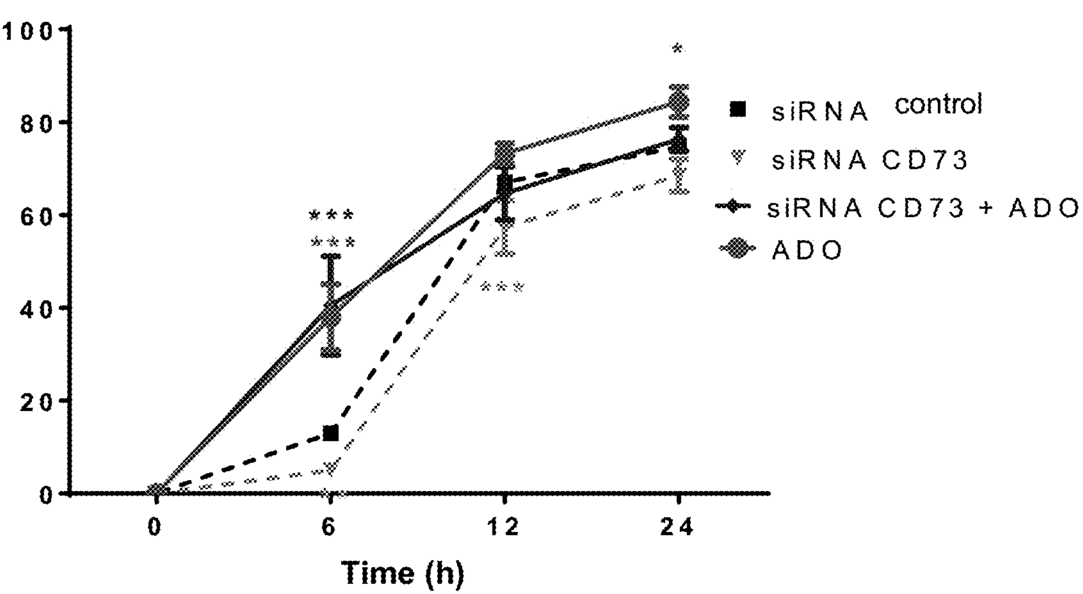
FIG. 14 indicates that CD73 silencing using the siRNA-CD73-441 sequence reduces cell migration of the human glioblastoma lineage U87MG.

The migration assay indicates that adenosine induced a sustained migration of U87MG glioma cells during the 24 hours of analysis. CD73 silencing using the siRNA-CD73-441 sequence (FIG. 14) impaired glioma cell migration, whereas adenosine treatment promoted recovery of the migratory potential of glioblastoma cells.

What is claimed is:

1. A nanometric pharmaceutical composition in the form of liposomes or a nanoemulsion containing interference RNA strands comprising one or more of the following specific siRNA sequences:

SEQ ID NO: 1;

SEQ ID NO: 2; or

SEQ ID NO: 3.

2. The composition of claim 1, wherein the composition is used to treat glioblastoma.

3. The composition of claim 1, comprising the interference RNA strands formed by SEQ ID NO: 1, SEQ ID NO: 2, and SEQ ID NO: 3 present a sense and antisense strand comprised of 19 nucleotides in an inverted orientation, separated by a space of 1 base pair.

4. The composition of claim 1, comprising a pharmaceutically acceptable excipient capable of carrying siRNA SEQ ID NO: 1, SEQ ID NO: 2, and SEQ ID NO: 3.

5. The composition of claim 4, wherein the pharmaceutically acceptable excipient is in the form of a liposome complex or nanoemulsion.

6. The composition of claim 1, wherein the nanoemulsion is composed of 8% (w/w) of medium chain triglycerides, 2% (w/w) of egg lecithin, 0.132% (w/w) of DOTAP (N-[1-(2, 3-dioleoyloxy) propyl]-N, N, Ntrimethylammonium methylsulfate, 2.25% (w/w) glycerol and water to complete 100% (w/w).

7. The composition of claim 1, wherein the nanoemulsion undergoes a process of transfection of the interfering RNA of SEQ ID NO: 1, SEQ ID NO: 2, and SEQ ID NO: 3.

8. The composition of claim 1, wherein the composition is a drug to silence genes responsible for the expression of overexposed proteins in glioblastoma.

9. The composition of claim 8, wherein the gene silenced by SEQ ID NO: 1 and SEQ ID NO: 2 is 58813/NT5E, and the gene silenced by SEQ ID NO:3 is 4907/NT5E.

10. The composition of claim 1, wherein a protein to be regulated is ecto-5'-nucleotidase/CD73.

11. The composition of claim 1, wherein the composition is administered intratumoral, parenteral, aerosol, oral, dermal, intradermal, inhalation, intramuscular injection, intranasal, intraocular, intrapulmonary, intravenous, intraperitoneal, nasal, ocular, optical, plaster, subcutaneous, sublingual, topical, or transdermal.

12. The composition of claim 10 wherein the composition is used in gene silencing kits.

13. A method for the treatment of glioblastoma comprising the step of administering to a patient an effective amount of the composition of claim 1.

14. A process for manufacturing a drug, wherein the process comprises forming a cationic nanometric lipid formulation and associating therewith an siRNA consisting of SEQ ID NO: 3 under conditions effective to form an electrostatic complex for treating a disease characterized by elevated CD73 expression.

15. The process of claim 14, wherein the process comprises combining SEQ ID NO:3 with a pharmaceutically acceptable carrier selected from the group consisting of a liposome complex and nanoemulsion, to produce the drug.

16. A method of using the drug produced by the process of claim 15 for treating a tumor, wherein the drug is administered via a route selected from the group consisting of intratumoral, parenteral, aerosol, oral, dermal, intradermal injection, inhalation, intramuscular, intranasal, intraocular, intrapulmonary, intravenous, intraperitoneal, nasal, ocular, otic, patch, subcutaneous, sublingual, topical, and transdermal.

17. The composition of claim 2, comprising a pharmaceutically acceptable excipient capable of carrying siRNA SEQ ID NO: 1, SEQ ID NO: 2, and SEQ ID NO: 3.

18. The composition of claim 3, comprising a pharmaceutically acceptable excipient capable of carrying siRNA SEQ ID NO: 1, SEQ ID NO: 2, and SEQ ID NO: 3.

19. The process of claim 14, wherein the disease is selected from the group consisting of tumors, glioblastoma, multiple sclerosis, and sepsis.

20. The method of claim 16, wherein the tumor is a glioma.

* * * * *

SEQUENCE LISTING

```
Sequence total quantity: 4
SEQ ID NO: 1           moltype = RNA  length = 42
FEATURE                Location/Qualifiers
misc_feature           1..42
                       note = RNA of interference sequence
source                 1..42
                       mol_type = other RNA
                       organism = synthetic construct
SEQUENCE: 1
gccatcaaag cagacattaa ctaatgtctg ctttgatggc tg                    42

SEQ ID NO: 2           moltype = RNA  length = 42
FEATURE                Location/Qualifiers
misc_feature           1..42
                       note = RNA of interference sequence
source                 1..42
                       mol_type = other RNA
                       organism = synthetic construct
SEQUENCE: 2
accagtggag gataaaatta gaattttatc ctccactggt ta                    42

SEQ ID NO: 3           moltype = RNA  length = 42
FEATURE                Location/Qualifiers
misc_feature           1..42
                       note = RNA of interference sequence
source                 1..42
                       mol_type = other RNA
                       organism = synthetic construct
SEQUENCE: 3
ggggccacta gcatctcaaa tttgagatgc tagtggcccc tt                    42

SEQ ID NO: 4           moltype = RNA  length = 38
FEATURE                Location/Qualifiers
misc_feature           1..38
                       note = RNA of interference sequence
source                 1..38
                       mol_type = other RNA
                       organism = synthetic construct
SEQUENCE: 4
caggctactt ggagtgtata tacactccaa gtagcctg                         38
```